United States Patent
Momtaz et al.

(10) Patent No.: US 10,961,350 B2
(45) Date of Patent: Mar. 30, 2021

(54) POLYMER COMPOSITION AND STERILIZABLE ARTICLES OBTAINABLE THEREFROM

(71) Applicant: SOLVAY SPECIALTY POLYMERS USA, LLC, Alpharetta, GA (US)

(72) Inventors: Maryam Momtaz, Hamme-Mille (BE); Corinne Bushelman, Cumming, GA (US)

(73) Assignee: SOLVAY SPECIALTY POLYMERS USA, INC., Alpharetta, GA (US)

(*) Notice: Subject to any disclaimer, the term of this patent is extended or adjusted under 35 U.S.C. 154(b) by 0 days.

(21) Appl. No.: 15/580,562

(22) PCT Filed: Jun. 7, 2016

(86) PCT No.: PCT/EP2016/062837
§ 371 (c)(1),
(2) Date: Dec. 7, 2017

(87) PCT Pub. No.: WO2016/198372
PCT Pub. Date: Dec. 15, 2016

(65) Prior Publication Data
US 2018/0134849 A1    May 17, 2018

Related U.S. Application Data

(60) Provisional application No. 62/173,632, filed on Jun. 10, 2015.

(51) Int. Cl.
| | | |
|---|---|---|
| *C08G 75/23* | (2006.01) |
| *C08L 81/06* | (2006.01) |
| *C08L 81/00* | (2006.01) |
| *A61L 2/14* | (2006.01) |
| *C08K 3/22* | (2006.01) |
| *C08L 79/08* | (2006.01) |

(52) U.S. Cl.
CPC ............. *C08G 75/23* (2013.01); *A61L 2/14* (2013.01); *C08K 3/22* (2013.01); *C08L 79/08* (2013.01); *C08L 81/00* (2013.01); *C08L 81/06* (2013.01); *A61L 2202/24* (2013.01); *C08K 2003/222* (2013.01); *C08K 2003/2206* (2013.01); *C08K 2003/2217* (2013.01); *C08K 2003/2227* (2013.01); *C08K 2003/2241* (2013.01); *C08K 2201/014* (2013.01)

(58) Field of Classification Search
CPC ....... C08G 75/23; A61L 2/14; A61L 2202/24; C08K 3/22; C08K 2003/2241; C08K 2201/014; C08K 2003/2217; C08K 2003/2206; C08K 2003/222; C08K 2003/2227; C08L 79/08; C08L 81/00; C08L 81/06
See application file for complete search history.

(56) References Cited

U.S. PATENT DOCUMENTS

| | | | |
|---|---|---|---|
| 4,643,876 A | 2/1987 | Jacobs et al. | |
| 5,204,400 A | 4/1993 | Kelly et al. | |
| 5,916,958 A * | 6/1999 | Kelly | C08G 75/23 |
| | | | 524/497 |
| 6,124,390 A * | 9/2000 | Nagashima | C08K 3/22 |
| | | | 524/425 |
| 6,365,102 B1 * | 4/2002 | Wu | A61L 2/14 |
| | | | 422/23 |
| 6,787,179 B2 * | 9/2004 | Timm | A61L 2/14 |
| | | | 427/2.24 |
| 8,501,291 B2 | 8/2013 | Davis et al. | |
| 8,945,694 B2 * | 2/2015 | Aneja | C08L 71/10 |
| | | | 428/35.7 |
| 2003/0022964 A1 | 1/2003 | Gallucci | |
| 2007/0037928 A1 * | 2/2007 | Weinberg | C08L 81/06 |
| | | | 525/189 |
| 2007/0197739 A1 * | 8/2007 | Aneja | C08L 2666/20 |
| | | | 525/437 |
| 2008/0064801 A1 * | 3/2008 | El-Hibri | C08K 5/09 |
| | | | 524/394 |
| 2008/0206536 A1 | 8/2008 | Weinberg | |
| 2009/0048379 A1 | 2/2009 | Weinberg et al. | |
| 2010/0310804 A1 * | 12/2010 | Bhatnagar | C08G 75/23 |
| | | | 428/36.9 |
| 2011/0294912 A1 | 12/2011 | Weber et al. | |
| 2012/0308777 A1 * | 12/2012 | Davis | C08L 79/08 |
| | | | 428/156 |
| 2013/0128361 A1 * | 5/2013 | Okaniwa | G02B 5/22 |
| | | | 359/580 |
| 2014/0170255 A1 | 6/2014 | Amend et al. | |
| (Continued) | | | |

FOREIGN PATENT DOCUMENTS

| | | | |
|---|---|---|---|
| EP | 1884538 A1 | 2/2008 | |
| EP | 3004227 A1 * | 4/2016 | ........... H05K 1/0353 |

(Continued)

OTHER PUBLICATIONS

Murphy J., in "Additives for Plastics Handbook", 2nd Edition, 2001, Chapter 5.2.3., p. 43-48—Elsevier Advanced Technology.
ASTM E308-08, "Standard Practice for Computing the Colors of Objects by Using the CIE System", p. 1-34, ASTM International, West Conshohocken, PA, 2008.

*Primary Examiner* — Pamela H Weiss

(57) ABSTRACT

The invention relates to a composition [composition (C)] comprising a poly(biphenyl ether sulfone) polymer [polymer (P)] and selected metal oxides in specific amounts. Composition (C) can be advantageously used for the manufacture of sterilizable shaped articles.

20 Claims, No Drawings

(56) References Cited

U.S. PATENT DOCUMENTS

2014/0353543 A1* 12/2014 Wu .......................... C08K 5/20
                                                                252/75
2016/0355679 A1* 12/2016 Aepli ..................... C08L 77/06

FOREIGN PATENT DOCUMENTS

| WO | 2006037773 A1 | 4/2006 | | |
|----|---------------|--------|---|---|
| WO | 2007107519 A1 | 9/2007 | | |
| WO | 2013092492 A1 | 6/2013 | | |
| WO | 2013092628 A1 | 6/2013 | | |
| WO | 2014202673 A1 | 12/2014 | | |
| WO | WO-2014195889 A1 * | 12/2014 | ........... | H05K 1/0353 |

* cited by examiner

POLYMER COMPOSITION AND STERILIZABLE ARTICLES OBTAINABLE THEREFROM

CROSS-REFERENCE TO RELATED APPLICATIONS

This application claims priority to U.S. provisional application No. 62/173,632 filed on 10 Jun. 2015, the whole content of this application being incorporated herein by reference for all purposes.

TECHNICAL FIELD

The present invention relates to a polymer composition comprising an aromatic polysulfone, namely a poly(biphenyl ether) sulfone, and to sterilizable articles obtainable from said composition.

BACKGROUND ART

Different methods of sterilization are available on the market for the elimination of transmissible agents such as fungi, bacteria and viruses. They are usually classified under heat, chemical or radiation sterilization processes. Among them, the high temperature steam sterilization and the low temperature hydrogen peroxide gas plasma sterilization methods are widely used today in the medical field.

The hydrogen peroxide gas plasma sterilization method, disclosed in U.S. Pat. No. 4,643,876 (SURGIKOS INC [US]), exploits the synergism between hydrogen peroxide and low temperature gas plasma, thereby allowing effective sterilization at about 50° C., which is significantly lower than that achieved in high temperature autoclave sterilization. Therefore, hydrogen peroxide gas plasma sterilization represents a valuable alternative to autoclave sterilization of medical articles comprising parts or devices (e.g. electronic or optical parts or devices) that do not withstand high temperatures or high moisture environments.

In the hydrogen peroxide gas plasma sterilization method, a medical article to be sterilized is placed into a closed plasma chamber wherein vacuum is applied and a solution of hydrogen peroxide is injected at a sufficient pressure to allow contact between the solution and the article. Thereafter, hydrogen peroxide gas plasma is generated for a time allowing complete sterilization.

The advantage of hydrogen peroxide gas plasma sterilization is that sterilization is completed in a relative short time, so the articles can be subjected to more sterilization cycles; however, due to the harsh oxidizing power of hydrogen peroxide and to the fact that an ionized acidic vapor is formed, certain articles, especially plastic articles, undergo deterioration of their properties and appearance. For example, commercially available articles made from polyphenyl sulfones (PPSU) compositions have an outstanding resistance to steam sterilization but a low resistance to hydrogen peroxide gas plasma sterilization: their color turns to orange and a slight decrease in the molecular weight of the (PPSU) is observed after a high number of cycles.

U.S. Pat. No. 8,501,291 (SABIC INNOVATIVE PLASTICS IP B.V) discloses a sterilized article comprising a hydrogen peroxide plasma or hydrogen peroxide vapor sterilized polymer composition, the polymer composition comprising:
from 20 to 80 weight percent of a polyphenylene ether sulfone; and
from 20 to 80 weight percent of a polyetherimide.

When sterilized with a hydrogen peroxide plasma, or hydrogen peroxide vapor, the articles are said to have surprisingly improved resistance to changes in color and clarity, as well as resistance to loss of mechanical properties with respect to compositions comprising only a polyphenylene ether sulfone.

The polyphenylene ether sulfone/polyetherimide composition may include several optional ingredients, among them fillers or reinforcing agents (col. 11, lines 48-49); titanium dioxide ($TiO_2$), aluminum oxide and magnesium oxide are cited in the description as examples of fillers or reinforcing agents (col. 11, lines 55-56). In the compositions of the examples, only $TiO_2$ is used.

Other patent documents, such as U.S. Pat. No. 5,204,400 (AMOCO CORP) (herein after "US '400"), US 2008064801 (SOLVAY ADVANCED POLYMERS LLC) (herein after "'US '801"), US 20080206536 (SOLVAY ADVANCED POLYMERS), US 2009048379 (SOLVAY ADVANCED POLYMERS LLC) (herein after "US '379") and WO 2014/170255 (SOLVAY SPECIALTY POLYMERS USA) (herein after "WO '255") disclose polymer compositions comprising poly(biphenyl ether sulfone) and metal oxides. In particular, US '801 and US '379 mention, inter alia, MgO and US '801 further mentions CaO; nevertheless, none of such documents recognizes or addresses the problem of increasing the resistance of compositions made from poly(biphenyl ether sulfone) to sterilization, in particular the problem of avoiding discoloration, and none of such documents provides hints or suggestions to the selection of a particular oxide in order to solve such problem.

Therefore, there is currently a great need on the market to find polymer compositions that withstand the harsh environments of both the high temperature steam sterilization and the low temperature hydrogen peroxide gas plasma sterilization methods.

DISCLOSURE OF THE INVENTION

The Applicant has now surprisingly found that the resistance to sterilization of compositions comprising a poly (biphenyl ether sulfone), in particular the resistance to sterilization with hydrogen peroxide gas plasma sterilization, can be increased by adding one or more specific metal oxides. In particular, the Applicant has surprisingly found that, even in the absence of a polyetherimide, the compositions of the invention do not discolor after repeated cycles of hydrogen peroxide gas plasma sterilization.

Accordingly, the present invention relates to a composition [composition (C)] comprising:
(a) a poly(biphenyl ether sulfone) polymer [polymer (P)];
(b) calcium oxide (CaO) and/or (MgO), optionally in combination with other
metal oxides;
with the provisos that:
  CaO, alone or in combination with MgO and/or with other metal oxides is at least 1% wt. with respect to the weight of the composition;
  if composition (C) does not include CaO, the amount of MgO is at least 2% wt. with respect to the weight of the composition.

In exemplary embodiments, the composition (C) further comprises a polyether imide polymer [polymer (PEI)]. In some embodiments, composition (C) does not include the polyether imide polymer [polymer (PEI)].

The invention further relates to shaped articles [articles (A)] comprising composition (C) and to methods for the manufacture of composition (C) and of shaped articles (A).

General Definitions

For the sake of clarity, throughout the present application:
any reference to general definitions of polymer (P) and polymer (PEI) is intended to include each specific definition falling within the respective general definition, unless indicated otherwise;
the indeterminate article "a" in expressions like "a polymer (P)", "a polymer (PEI)", "a metal oxide" etc . . . is intended to mean "one or more", or "at least one" unless indicated otherwise;
the use of brackets "( )" before and after names, symbols or numbers identifying formulae or parts of formulae, e.g. "a polymer (P)", "a polymer (PEI)", etc . . . , has the mere purpose of better distinguishing that name, symbol or number from the rest of the text; thus, said parentheses could also be omitted;
when numerical ranges are indicated, range ends are included;
the term "halogen" includes fluorine, chlorine, bromine and iodine, unless indicated otherwise;
the adjective "aromatic" or "aryl" denotes any mono- or polynuclear cyclic group (or moiety) having a number of π electrons equal to 4n+2, wherein n is 0 or any positive integer;
the term "method" is used as synonym of process and vice-versa;
"a shaped article (A) obtainable from composition (C)" or "shaped articles (A) obtainable from composition (C)" is(are) a shaped article(s) comprising composition (C).

The Poly(Biphenyl Ether Sulfone) [Polymer P]

For the purpose of the present invention, the term "poly (biphenyl ether sulfone)" [polymer (P)] is intended to denote a polycondensation polymer wherein more than 50 wt. % of the recurring units are recurring units ($R_a$) including:
one or more moieties comprising at least one biphenylene group, preferably selected from the group consisting of formulae ($R_a$-1) to ($R_a$-3) here below:

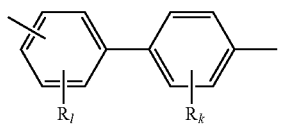
(Ra-1)

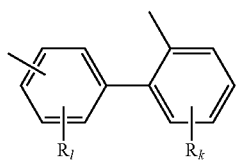
(Ra-2)

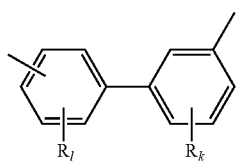
(Ra-3)

wherein:
R is selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium and j, k and l equal or different from each other, are independently 0, 1, 2, 3 or 4;
at least one ether group (—O—) and
at least one sulfone group (—SO$_2$—).

The recurring units ($R_a$) are advantageously recurring units of formula (A) here below:

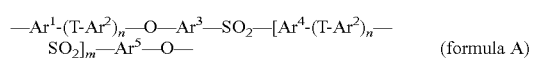
—Ar$^1$-(T-Ar$^2$)$_n$—O—Ar$^3$—SO$_2$—[Ar$^4$-(T-Ar$^2$)$_n$—SO$_2$]$_m$—Ar$^5$—O— (formula A)

wherein:
—Ar$^1$, Ar$^2$, Ar$^3$, Ar$^4$, and Ar$^5$, equal to or different from each other and at each occurrence, are independently an aromatic mono- or polynuclear cyclic group;
with the proviso that at least one Ar$^1$ through Ar$^5$ is an aromatic moiety comprising at least one biphenylene group selected from formulae ($R_a$-1) to ($R_a$-3) as defined above;
each of T, equal to or different from each other, is a bond or a divalent group optionally comprising one or more than one heteroatom;
n and m, equal to or different from each other, are independently zero or an integer of 1 to 5.

Preferably, Ar$^1$, Ar$^2$, Ar$^3$, Ar$^4$, Ar$^5$ are equal or different from each other and are aromatic moieties preferably selected from the group consisting of formulae ($R_a$-1) to ($R_a$-6):

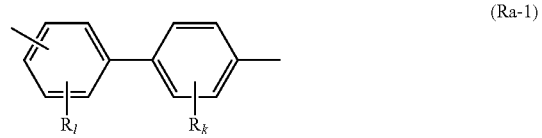
(Ra-1)

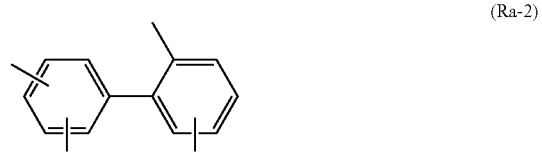
(Ra-2)

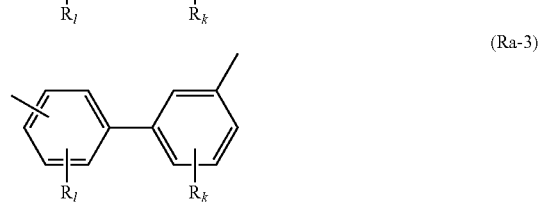
(Ra-3)

(Ra-4)

(Ra-5)

-continued (Ra-6)

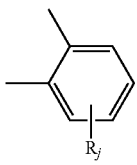

wherein:
R is as defined above;
j, k and l equal or different from each other, are independently 0, 1, 2, 3 or 4, and
with the proviso that at least one $Ar^1$ through $Ar^5$ is an aromatic moiety comprising at least one biphenylene group, selected from those complying with formulae ($R_a$-1) to ($R_a$-3) as defined above.

Preferably, each of T, equal to or different from each other, is selected from the group consisting of a bond, —$CH_2$—; —O—; —$SO_2$—; —S—; —C(O)—; —C($CH_3$)$_2$—; —C($CF_3$)$_2$—; —C(=$CCl_2$)—; —C($CH_3$) ($CH_2CH_2COOH$)—; —N=N—; —$R^1$C=C$R^2$—; wherein each $R^1$ and $R^2$, independently of one another, is hydrogen or a $C_1$-$C_{12}$-alkyl, $C_1$-$C_{12}$-alkoxy, or $C_6$-$C_{18}$-aryl group; —($CH_2$)$_n$ and —($CF_2$)$_n$— with n=integer from 1 to 6, or an aliphatic linear or branched divalent group of up to 6 carbon atoms.

More preferably, recurring units ($R_a$) are selected from the group consisting of formulae (B) to (F) illustrated below, and mixtures thereof:

(ii) recurring units ($R_a$) of one or more formulae (B) to (F) and recurring units ($R_a$*), different from recurring units ($R_a$), such as:

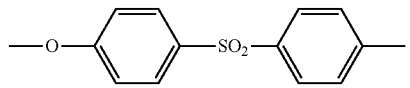
(G)

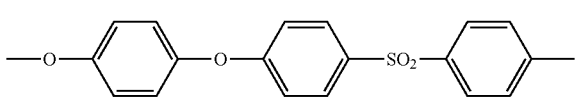
(H)

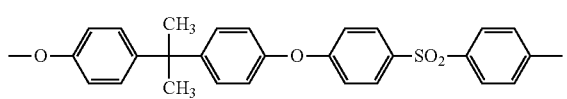
(I)

Preferably, more than 75 wt. %, preferably more than 85 wt. %, preferably more than 95 wt. %, preferably more than 99 wt. % of the recurring units of polymer (P) are recurring units ($R_a$).

Still, it is generally preferred that substantially all recurring units of polymer (P) are recurring units ($R_a$), as detailed above; chain defects, or very minor amounts of other units might be present, being understood that these latter do not substantially modify the properties of ($R_a$).

Polymer (P) is then preferably a polyphenylsulfone (PPSU).

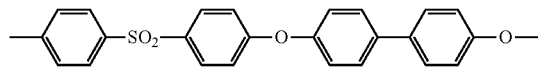
(B)

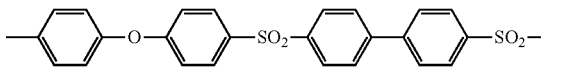
(C)

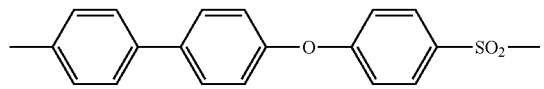
(D)

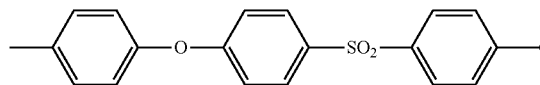
(E)

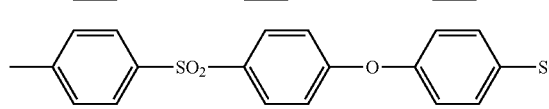
(F)

Most preferably, the recurring units ($R_a$) comply with formula (B):

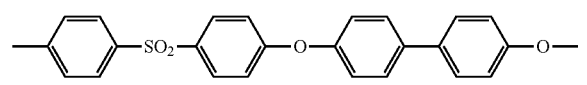
(B)

Polymer (P) may be notably a homopolymer, a random, alternate or block copolymer. When polymer (P) is a copolymer, its recurring units may notably be composed of:
(i) recurring units ($R_a$) of at least two different formulae selected from formulae (B) to (F), or For the purpose of the present invention, the term "polyphenylsulfone" [(PPSU) polymer] denotes any polymer of which more than 50 wt. % of the recurring units are recurring units ($R_a$) of formula (B).

In a preferred embodiment, more than 75 wt. % more preferably more than 90 wt. %, more preferably more than 99 wt. %, even more preferably all the recurring units of polymer (P) are of formula (B).

RADEL® PPSU from Solvay Specialty Polymers USA, L.L.C. is an example of a commercially available (PPSU) homopolymer.

The polymer (P) can be prepared by any method. The molecular weight of polymer (P), when determined as reduced viscosity in an appropriate solvent such as methylene chloride, chloroform, N-methylpyrrolidone, or the like, can be greater than or equal to 0.3 dl/g, or, more specifically, greater than or equal to 0.4 dl/g and, typically, will not exceed 1.5 dl/g.

The weight average molecular weight of polymer (P) can be 10,000 to 100,000 grams per mole (g/mol) as determined by gel permeation chromatography following ASTM D5296 standard, using polystyrene calibration curve. In some embodiments, the weight average molecular weight of polymer (P) can be 20,000 to 70,000 grams per mole (g/mol).

Polymer (P) may have glass transition temperatures of 180 to 250° C., when determined according to ASTM D 3418.

Calcium Oxide, Magnesium Oxides and Other Metal Oxides

CaO and MgO suitable for the manufacture of composition (C) have an average particle size up to about 5 microns and a BET surface area of 1.5-160 m²/g. Such CaO and MgO are available on the market.

Excellent results were obtained with CA602, a grade of calcium oxide from Atlantic Equipment Engineers, a division of Micron Metals, Inc.

Excellent results were also obtained with Kyowamag® MF-150, a grade of MgO from Kyowa Chemical Industry Co. Ltd.

For the purpose of the present invention, the expression "other metal oxides" is intended to denote a chemical compound selected from aluminum oxide ($Al_2O_3$), zinc oxide (ZnO) and mixtures thereof.

Composition (C) may comprise such other metal oxides in amounts ranging from 0.1% to 5% wt. with respect to the weight of the composition (C). Advantageously, the amount of the other metal oxide in composition (C) ranges from 0.15% to 3% wt.; more advantageously, the amount of the other metal oxide ranges from 0.2 to 2% wt.

The Polyether Imide (PEI)

For the purpose of the present invention, the term "polyether imide (PEI)" is intended to denote any polymer of which more than 50 wt. % of the recurring units [units ($R_b$)] comprise at least one aromatic ring, at least one imide group, as such and/or in its amic acid form, and at least one ether group [recurring units ($R_b$-1)].

Recurring units ($R_b$-1) may optionally further comprise at least one amide group which is not included in the amic acid form of an imide group.

The recurring units ($R_b$) are advantageously selected from the group consisting of following formulae (I), (II), (III), (IV) and (V), and mixtures thereof:

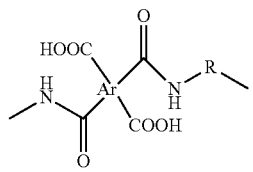

(I)

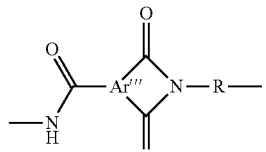

(II)

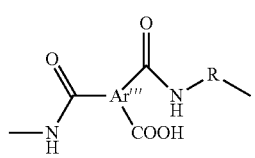

(III)

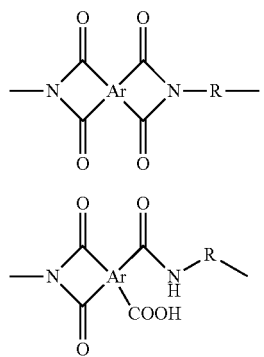

(IV)

(V)

wherein:
Ar is a tetravalent aromatic moiety and is selected from the group consisting of a substituted or unsubstituted, saturated, unsaturated or aromatic monocyclic and polycyclic group having 5 to 50 carbon atoms;
Ar''' is a trivalent aromatic moiety and is selected from the group consisting of a substituted or unsubstituted, saturated, unsaturated or aromatic monocyclic and polycyclic group having 5 to 50 carbon atoms and
R is selected from the group consisting of substituted or unsubstituted divalent organic radicals, and more particularly consisting of (a) aromatic hydrocarbon radicals having 6 to 20 carbon atoms and halogenated derivatives thereof; (b) straight or branched chain alkylene radicals having 2 to 20 carbon atoms; (c) cycloalkylene radicals having 3 to 20 carbon atoms, and (d) divalent radicals of the general formula (VI):

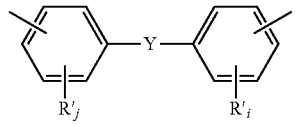

(VI)

wherein Y is selected from the group consisting of alkylenes of 1 to 6 carbon atoms, in particular —C(CH₃)₂ and —$C_nH_{2n}$— (n being an integer from 1 to 6); perfluoroalkylenes of 1 to 6 carbon atoms, in particular —C(CF₃)₂ and —$C_nF_{2n}$— (n being an integer from 1 to 6); cycloalkylenes of 4 to 8 carbon atoms; alkylidenes of 1 to 6 carbon atoms; cycloalkylidenes of 4 to 8 carbon atoms; —O—; —S—; —C(O)—; —SO₂—; —SO—, and R' is selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium and i and j, equal or different from each other, are independently 0, 1, 2, 3 or 4, with the proviso that at least one of Ar, Ar''' and R comprise at least one ether group.

Preferably, Ar is selected from the group consisting of the following formulae:

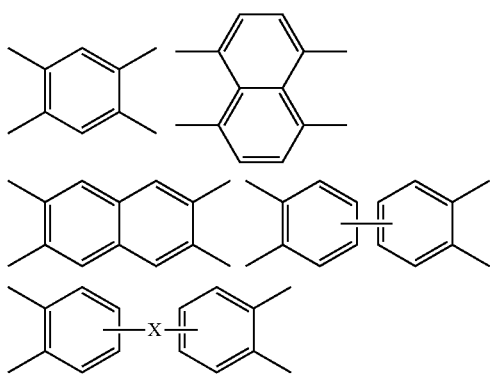

wherein X is a divalent moiety, having divalent bonds in the 3,3', 3,4', 4,3" or the 4,4' positions and is selected from the group consisting of alkylenes of 1 to 6 carbon atoms, in particular —C(CH$_3$)$_2$— and —C$_n$H$_{2n}$— (n being an integer from 1 to 6); perfluoroalkylenes of 1 to 6 carbon atoms, in particular —C(CF$_3$)$_2$— and —C$_n$F$_{2n}$— (n being an integer from 1 to 6); cycloalkylenes of 4 to 8 carbon atoms; alkylidenes of 1 to 6 carbon atoms; cycloalkylidenes of 4 to 8 carbon atoms; —O—; —S—; —C(O)—; —SO$_2$—; —SO—, or X is a group of the formula O—Ar'"—O; and wherein Ar'" is selected from the group formulae (VII) to (XIII), and mixtures thereof:

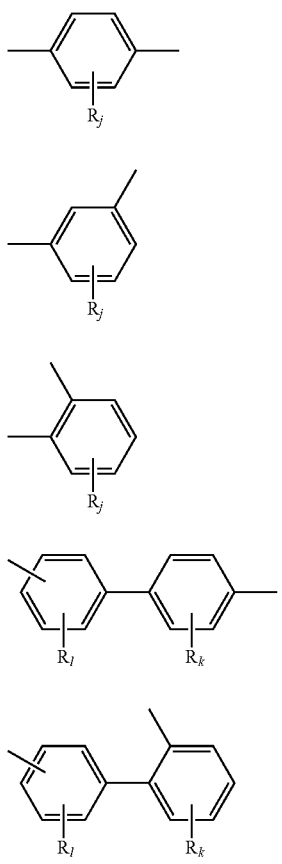

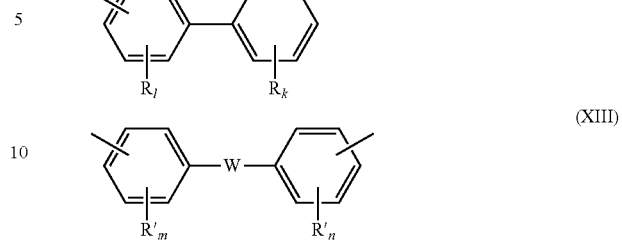

wherein R and R', equal or different from each other, are independently selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium and j, k, l, n and m equal or different from each other, are independently 0, 1, 2, 3 or 4, and W is selected from the group consisting of alkylenes of 1 to 6 carbon atoms, in particular —C(CH$_3$)$_2$— and —C$_n$H$_{2n}$— (with n being an integer from 1 to 6); perfluoroalkylenes of 1 to 6 carbon atoms, in particular —C(CF$_3$)$_2$— and —CnF$_{2n}$— (with n being an integer from 1 to 6); cycloalkylenes of 4 to 8 carbon atoms; alkylidenes of 1 to 6 carbon atoms; cycloalkylidenes of 4 to 8 carbon atoms; —O—; —S—; —C(O)—; —SO$_2$—; and —SO—.

Preferably, Ar'" is selected from the group consisting of the following formulae:

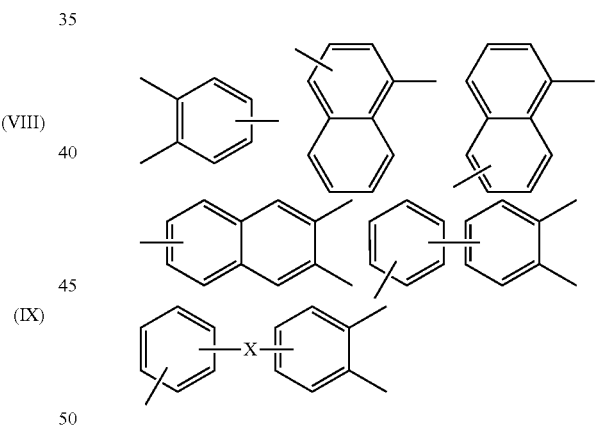

wherein X has the same meaning as above.

In a preferred embodiment, the recurring units (R$_b$-1) are selected from the group consisting of units of formula (XIV) in imide form, of corresponding units in amic acid forms of formulae (XV) and (XVI), and of mixtures thereof;

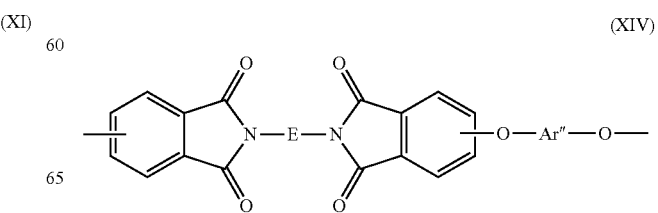

(XV)

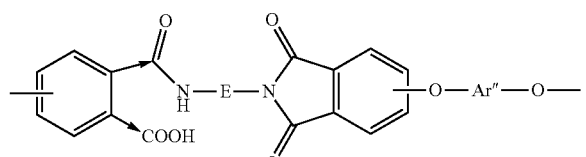

(XVI)

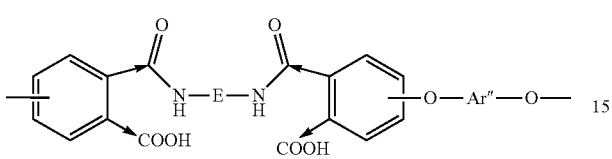

wherein:
the → denotes isomerism so that in any recurring unit the groups to which the arrows point may exist as shown or in an interchanged position;

Ar" is selected from the group consisting of formulae (VII) to (XIII)

(VII)

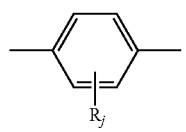

(VIII)

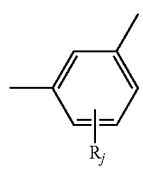

(IX)

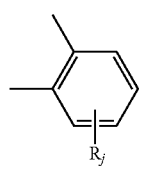

(X)

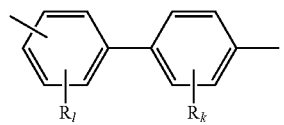

(XI)

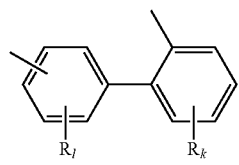

(XII)

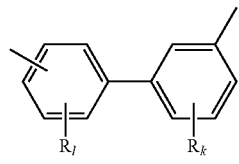

(XIII)

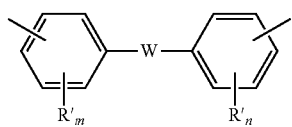

wherein R and R', equal or different from each other, are independently selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium and j, k, l, n and m equal or different from each other, are independently 0, 1, 2, 3 or 4, and W is selected from the group consisting of alkylenes of 1 to 6 carbon atoms, in particular —C(CH$_3$)$_2$— and —C$_n$H$_{2n}$— (n being an integer from 1 to 6); perfluoroalkylenes of 1 to 6 carbon atoms, in particular —C(CF$_3$)$_2$— and —C$_n$F$_{2n}$— (n being an integer from 1 to 6); cycloalkylenes of 4 to 8 carbon atoms; alkylidenes of 1 to 6 carbon atoms; cycloalkylidenes of 4 to 8 carbon atoms; —O—; —S—; —C(O)—; —SO$_2$—; and —SO—;

E is selected from the group consisting of —C$_n$H$_{2n}$— (n being an integer from 1 to 6), divalent radicals of the general formula (VI), as defined above, and those complying with formulae (XVII) to (XXII)

(XVII)

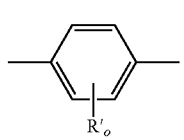

(XVIII)

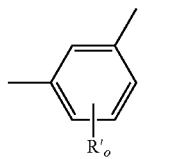

(XIX)

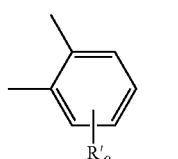

(XX)

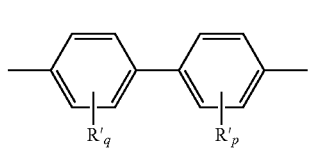

(XXI)

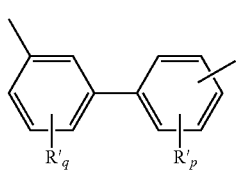

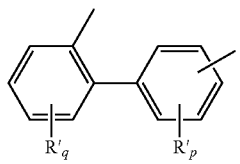

(wherein R' is selected from the group consisting of: hydrogen, halogen, alkyl, alkenyl, alkynyl, aryl, ether, thioether, carboxylic acid, ester, amide, imide, alkali or alkaline earth metal sulfonate, alkyl sulfonate, alkali or alkaline earth metal phosphonate, alkyl phosphonate, amine and quaternary ammonium and o, p, and q equal or different from each other, are independently 0, 1, 2, 3 or 4.

Preferably, E is selected from the group consisting of formulae (XVII) to (XIX), as defined above; more preferably, E is selected from the group consisting of unsubstituted m-phenylene and unsubstituted p-phenylene, and mixtures thereof.

Preferably, Ar" is complies with general formula (XIII), as detailed above; more preferably, Ar" is

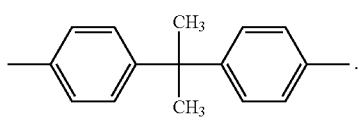

The polymer (PEI) wherein the recurring units ($R_b$-1) are recurring units of formula (XIV) as such, in imide form, and/or in amic acid forms [formulae (XV) and (XVI)], as defined above, can be prepared by any method well-known to those skilled in the art including the reaction of an aromatic bis(ether anhydride) of the formula:

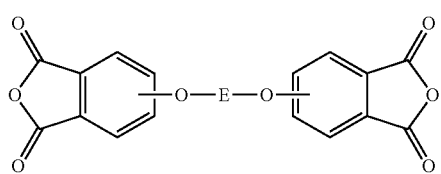

(XXIII)

wherein E is as defined above,
with a diamino compound of the formula:

H$_2$N—Ar"—NH$_2$      (XXIV)

wherein Ar" is as defined above. In general, the reactions can be advantageously carried out in well-known solvents, e.g., o-dichlorobenzene, m-cresol/toluene, N,N-dimethylacetamide, etc., in which interaction between the dianhydrides and diamines can occur, at temperatures of from about 20° C. to about 250° C.

Alternatively, these polymers (PEI) can be prepared by melt polymerization of a dianhydride of formula (XXIII) with a diamino compound of formula (XXIV), while heating the mixture of the ingredients at elevated temperatures with concurrent intermixing.

The aromatic bis(ether anhydride)s of formula (XXIII) include, for example:
2,2-bis[4-(2,3-dicarboxyphenoxy)phenyl]propane dianhydride;
4,4'-bis(2,3-dicarboxyphenoxy)diphenyl ether dianhydride;
1,3-bis(2,3-dicarboxyphenoxy)benzene dianhydride;
4,4'-bis(2,3-dicarboxyphenoxy)diphenyl sulfide dianhydride;
1,4-bis(2,3-dicarboxyphenoxy)benzene dianhydride;
4,4'-bis(2,3-dicarboxyphenoxy)benzophenone dianhydride;
4,4'-bis(2,3-dicarboxyphenoxy)diphenyl sulfone dianhydride;
2,2-bis[4 (3,4-dicarboxyphenoxy)phenyl]propane dianhydride;
4,4'-bis(3,4-dicarboxyphenoxy)diphenyl ether dianhydride;
4,4'-bis(3,4-dicarboxyphenoxy)diphenyl sulfide dianhydride;
1,3-bis(3,4-dicarboxyphenoxy)benzene dianhydride;
1,4-bis(3,4-dicarboxyphenoxy)benzene dianhydride;
4,4'-bis(3,4-dicarboxyphenoxy)benzophenone dianhydride;
4-(2,3-dicarboxyphenoxy)-4'-(3,4-dicarboxyphenoxy)diphenyl-2,2-propane dianhydride;
and mixtures thereof.

The organic diamines of formula (XXIV) include, for example, m-phenylenediamine, p-phenylenediamine, 2,2-bis(p-aminophenyl)propane, 4,4'-diaminodiphenyl-methane, 4,4'-diaminodiphenyl sulfide, 4,4'-diamino diphenyl sulfone, 4,4'-diaminodiphenyl ether, 1,5-diaminonaphthalene, 3,3'-dimethylbenzidine, 3,3'-dimethoxybenzidine, and mixtures thereof.

In a preferred embodiment, the organic diamine of formula (XXIV) is selected from the group consisting of m-phenylenediamine and p-phenylenediamine and mixture thereof.

In a most preferred embodiment, the recurring units ($R_b$-1) are recurring units selected from formula (XXV) in imide form, its corresponding amic acid forms of formulae (XXVI) and (XXVII), and mixtures thereof:

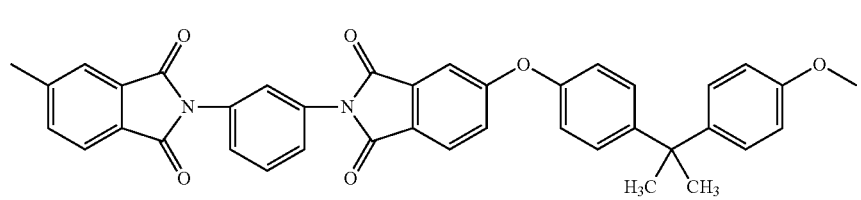

(XXV)

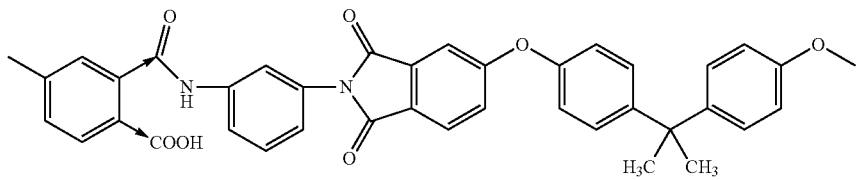

(XXVI)

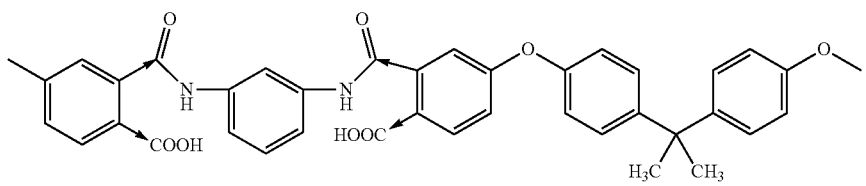

(XXVII)

wherein in formulae (XXVI) and (XXVII) the → denotes isomerism so that in any recurring unit the groups to which the arrows point may exist as shown or in an interchanged position.

In another most preferred embodiment, the recurring units ($R_b$-1) are recurring units selected from formula (XXVIII) in imide form, its corresponding amic acid forms of formulae (XXIX) and (XXX), and mixtures thereof:

formula (XXV), their corresponding amic acid forms of formulae (XXVI) and (XXVII), and mixtures thereof.

In another preferred embodiment of the present invention, more than 75 wt. % more preferably more than 90 wt. %, more preferably more than 99 wt. %, even more preferably all the recurring units of the polymer (PEI) are recurring units selected from the group consisting of those in imide form of formula (XXVIII), their corresponding amic acid

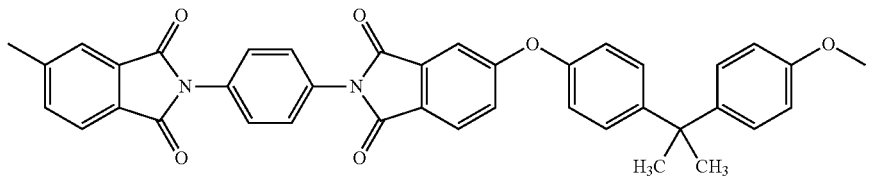

(XXVIII)

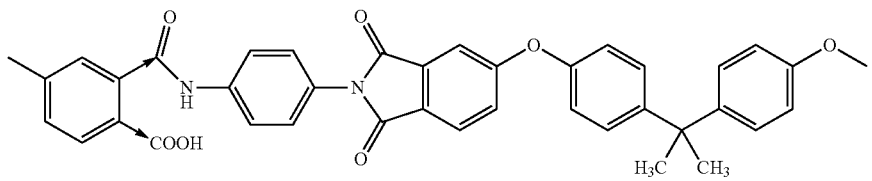

(XXIX)

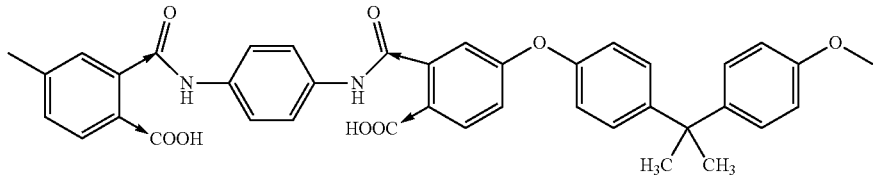

(XXX)

wherein in formulae (XXIX) and (XXX) the → denotes isomerism so that in any recurring unit the groups to which the arrows point may exist as shown or in an interchanged position.

Preferably, more than 75 wt. % and more preferably more than 90 wt. % of the recurring units of the polymer (PEI) are recurring units ($R_a$). Still more preferably, essentially all, if not all, the recurring units of the polymer PEI are recurring units ($R_a$).

In a preferred embodiment of the present invention, more than 75 wt. % more preferably more than 90 wt. %, more preferably more than 99 wt. %, even more preferably all the recurring units of the polymer (PEI) are recurring units selected from the group consisting of those in imide form of forms of formulae (XXIX) and (XXX), and mixtures thereof. Such polymers (PEI) are notably commercially available from Sabic Innovative Plastics as ULTEM™ polyetherimides.

Generally, polymers (PEI) useful in the present invention have a melt index of 0.1 to 10 grams per minute (g/min), as measured according to ASTM D1238 at 295° C., using a 6.6 kilogram (kg) weight.

In a specific embodiment, the polymer (PEI) has a weight average molecular weight (Mw) of 10,000 to 150,000 grams per mole (g/mole), as measured by gel permeation chromatography, using a polystyrene standard. Such polymer (PEI) typically has an intrinsic viscosity greater than 0.2 deciliters per gram (dl/g), beneficially 0.35 to 0.7 dl/g measured in m-cresol at 25° C.

Optional Ingredients in Composition (C)

In addition to or instead of polymer (PEI), the composition (C) can comprise one or more other polymers such as polyacetal, ethylvinyl acetate (EVA), polyolefins, liquid crystal polymers (LCP), polyamides, polycarbonates, poly (etherketones) (PEK), poly(etheretherketones) (PEEK), poly(etherketoneketones) (PEKK), polymethyl methacrylate (PMMA), polystyrene, polyurethane, polyvinyl chloride (PVC), silicone elastomers, polytetrafluoroethylene and mixtures thereof.

Composition (C) may also include further ingredients, such as fillers (or reinforcing agent), antioxidants, mold-releasing agents, stabilizers and biocidal compounds.

Non-limiting examples of fillers include silicates and silica powders, boron powders, calcium sulfate and calcium carbonates, talc, kaolin and glass fibers. Non-limiting examples of glass fibers are A, C, D, E, M, S, R, T glass fibers (as described in chapter 5.2.3, pages 43-48 of *Additives for Plastics Handbook*, $2^{nd}$ ed, John Murphy) and mixtures thereof.

Non-limiting examples of antioxidants include phenols, phosphites and phosphonites.

Non-limiting examples of mold-releasing agents include waxes, natural and synthetic paraffins, fluorocarbons, amides of fatty acids, in particular stearamide.

Non-limiting examples of stabilizers include phosphorous-including stabilizers, such as aryl phosphites and aryl phosphonates.

Non-limiting examples of biocidal agents include one or more of metals, advantageously silver, zinc and copper and mixtures thereof, and other inorganic or inorganic compounds known in the art endowed with antimicrobial, antibiotic, antibacterial, germicidal, antiviral, antifungal, antiparasite, antiyeast, antialgae and antiprotozoal activity or a combination of such activities.

Composition (C) may further comprise colorants selected from dyes and pigments. Non-limiting examples of pigments include titanium dioxide ($TiO_2$), carbon black and zinc sulfide. Very good results were obtained using $TiO_2$, preferably in an amount of 1-6% wt. with respect to the composition (C).

Composition (C), Article (A), and Methods for the Manufacture Thereof

Composition (C) comprises polymer (P) in an amount of at most 99% wt. with respect to the weight of the composition (C); advantageously, composition (C) comprises at most 98% wt., at most 97% wt., at most 96% wt., at most 95% wt., at most 94% wt. with respect to the weight of the composition (C). The amount of polymer (P) is at least 20% wt. with respect to the weight of the composition (C). Advantageously, the amount of polymer (P) is at least 30% wt., at least 50% wt., at least 60% wt., at least 80% wt., and at least 90% wt. with respect to the weight of the composition (C).

Composition (C) comprises CaO in amounts typically ranging from 1% to 6% wt. with respect to the weight of the composition (C); advantageously, the amount of CaO ranges from 2% to 5% wt., from 2% to 4% wt., from 2% to 3% wt., with respect to the weight of the composition (C), provided that, when CaO is present in combination with MgO and/or with another metal oxide, the amount of CaO is at least 1% wt. with respect to the weight of the composition (C).

Composition (C) comprises MgO in amounts typically ranging from 0.5% to 6% wt. with respect to the weight of the composition (C); advantageously, the amount of MgO ranges from 1% to 5% wt., from 1% to 4%, from 1 to 3% wt., from 1 to 2% wt. with respect to the weight of the composition (C), provided that, when composition (C) does not include CaO, the amount of MgO is at least 2% wt. with respect to the weight of the composition (C).

In one embodiment, composition (C) advantageously includes 4% CaO.

In another embodiment, composition (C) advantageously includes 2% wt. CaO and 2% wt. MgO.

In another embodiment, composition (C) advantageously includes 1% wt. CaO and 1% wt. MgO.

In another embodiment, composition (C) advantageously includes 4% wt. of a mixture of MgO and $Al_2O_3$.

Typically, when composition (C) includes both a polymer (P) and a polymer (PEI) and/or another polymer, such as one of those defined above, the amount of polymer (PEI) or such other polymer typically ranges from 20% wt. to 79% wt., preferably from 20% wt. to 74% wt., more preferably from 50% wt. to 70% wt., even more preferably about 60% wt., with respect to the weight of the composition (C).

Any other optional ingredients as indicated above can be present in composition (C) in amounts typically ranging from 1% to 50% wt. with respect to the weight of the composition (C).

In any case, very good results were obtained with a composition (C) and an article (A) obtainable therefrom that does not comprise any additional ingredient, i.e. a composition (C) consisting or consisting essentially of:

(a) a polymer (P) as defined above; and (b) CaO and/or MgO, optionally in combination other metal oxides, with the above provisos concerning the weight of CaO and MgO.

Excellent results were obtained with a composition (C) and an article (A) obtainable therefrom consisting or consisting essentially of:

(a) a polymer (P) as defined above, preferably a polymer (P) wherein all the recurring units are of formula (B) as defined above;

(b) CaO, preferably in an amount of 4% wt. with respect to the weight of the composition (C), preferably in an amount of 2%, with respect to the weight of the composition (C).

Excellent results were also obtained with a composition (C) and an article (A) obtainable therefrom consisting of or consisting essentially of:

(a) a polymer (P) as defined above, preferably a polymer (P) wherein all the recurring units are of formula (B) as defined above;

(b) CaO and MgO, preferably in an amount of 2% wt. each, more preferably in an amount of 1% wt. each.

Excellent results were also obtained with a composition (C) and an article (A) obtainable therefrom consisting of or consisting essentially of:

(a) a polymer (P) as defined above, preferably a polymer (P) wherein all the recurring units are of formula (B) as defined above;

(b) 4% wt. of a mixture of MgO and $Al_2O_3$.

The composition (C) of the present invention and article (A) obtainable therefrom can be manufactured by blending a polymer (P) as defined above, CaO and/or MgO and/or any other metal oxide and any optional additional ingredients as defined above in selected amounts, followed by processing according to methods known in the art, such as melt processing (including injection molding, extrusion molding, compression molding, blow molding and rotational molding) and solution processing.

Non-limiting examples of articles (A) are molded parts, sheets, slabs, profiles, films, and fibers. The articles (A) are preferably selected from medical articles, such as dental articles, surgical articles, food handling or food preparation articles, beverage handling or beverage preparation articles.

Such articles can notably be used as a component for the manufacture of a device selected from the group consisting of medical devices, dental devices, surgical devices, sterilization devices, decontamination devices, food handling devices, food preparation devices, beverage handling devices and beverage preparation.

Non-limiting examples of such articles are containers, boxes, animal cages, trays, latches, lids, bumpers, orthopedic trials, instrument handles, clamps, cables, scissors, forceps, catheters, tubes, prostheses, membranes, including medical articles that contain electronic or optical parts, like radiation therapy equipment, endoscopes, ophthalmic lenses and probes.

The composition (C) and articles (A) are able to withstand harsh conditions occurring during sterilization processes, in particular during $H_2O_2$ gas plasma sterilization processes; in particular, articles (A) retain their shape and mechanical properties and do not undergo discoloration. For the purpose of the present invention, the composition (C) or article (A) does not undergo discoloration when the overall color difference (DE) and the change in yellowness (Db) are less than 5.5. Advantageously, DE and Db are less than 4.5, less than, 2.7, less than 1.9, less than 1.3, less than 1.0, less than 0.7. DE and Db can be calculated according to known methods from the CIE 1976 (L*, a*, b*) color space indexes measured according to ASTM E308-08. In particular, (DE) can be calculated from the (L*, a*, b*) indexes according to the CIE94 formula.

Thus, in a further embodiment, the present invention comprises a method for manufacturing a sterilized shaped article obtained from composition (C), said method comprising submitting a shaped article (A) to high temperature or low temperature sterilization, in particular to $H_2O_2$ gas plasma sterilization. Excellent results were obtained by submitting an article (A) to 50 cycles of 47 minutes each of $H_2O_2$ gas plasma sterilization.

The invention will be herein after illustrated in greater detail in the following section by means of non-limiting examples.

Should the disclosure of any patents, patent applications, and publications which are incorporated herein by reference conflict with the description of the present application to the extent that it may render a term unclear, the present description shall take precedence.

EXPERIMENTAL SECTION

Starting Materials

Polymer-1: Radel® R-5100 NT, which is a polyphenylsulfone (PPSU) homopolymer from Solvay Specialty Polymers USA, L.L.C.

$TiO_2$-1: Titanium dioxide rutile R105 from Dupont Titanium technologies $TiO_2$-2: KRONOS® 2233 from Kronos Inc.

MgO: Kyowamag® MF-150 is a grade of magnesium oxide from Kyowa Chemical Industry Co. Ltd.

KW-2200 is a mixture of metal oxides (~35% $Al_2O_3$ and ~60% MgO) from Kyowa Chemical Industry Co. Ltd.

CaO: CA602 is a grade of calcium oxide from Atlantic Equipment Engineers, a division of Micron Metals, Inc.

General Procedure for the Preparation of the Compositions

All of the ingredients were fed in the first barrel of a ZSK-26 twin-screw extruder comprising twelve zones via several weight and loss feeders. The screw rate was 200 rpm. The barrel settings were in the range 340-360° C. The extrudates were cooled and pelletized using conventional equipment.

The nature and the quantity of the various components are summarized in Tables 1a and 1b, indicating the amount of each ingredient in weight %.

TABLE 1a

Ingredients of the tested compositions

|  | CE1 | CE2 | CE3 |
|---|---|---|---|
| Polymer-1 | 98 | 96 | 97 |
| $TiO_2$-1 | 2 |  | 2 |
| $TiO_2$-2 |  | 2 |  |
| CaO |  |  |  |
| MgO |  |  | 1 |
| KW 2200 |  | 2 |  |

CE = comparative example
E = example according to the invention

TABLE 1b

Ingredients of the tested compositions

|  | E1 | E2 | E3 | E4 | E5 | E6 | E7 | E8 | E9 | E10 | E11 |
|---|---|---|---|---|---|---|---|---|---|---|---|
| Polymer-1 | 97 | 96 | 96 | 94 | 94 | 96 | 95 | 94 | 94 | 96 | 94 |
| $TiO_2$-1 | 2 |  | 2 | 2 | 2 | 2 | 2 | 2 |  | 2 | 2 |
| $TiO_2$-2 |  | 2 |  |  |  |  |  |  | 2 |  |  |
| CaO | 1 | 1 | 2 | 4 | 2 | 1 | 2 | 3 |  |  |  |
| MgO |  |  |  |  | 2 | 1 | 1 | 1 |  | 2 | 4 |
| KW 2200 |  | 1 |  |  |  |  |  |  | 4 |  |  |

E = example according to the invention

General Procedure for the Sterilization of the Samples

The compositions reported in Tables 1a and 1b were injection molded into color chips. The color chips were loaded and cycled in a STERRAD® 100NX low temperature hydrogen peroxide sterilization chamber (manufactured by Advanced Sterilization Products, Division of Ethicon Inc.) to evaluate the samples ability to retain their white color. Each sample was run for 50 cycles of sterilization of 47 minutes each.

Color Measurement

The L, a and b values were measured on color chips using a CE7000 Gretag MacBeth spectrophotometer using Cool White Fluorescent (F2) illuminant, a 10° observer, a 10 nm wavelength interval, a spectral range of from 360 to 700 nm and a D/8 optical geometry configuration with a band pass correction using table 5.27 of the ASTM E 308-08 (on page 22). The reported values are the average of five measurements made on five different color chips.

The overall color difference (ΔE) and the change in yellowness (Δb) between the specimens exposed to 50 cycles of STERRAD sterilization cycles of 47 minutes each and the control specimens was characterized by CIE94 ΔE and according to the color measurement method described above. They are presented in Tables 2a and 2b.

TABLE 2a

Results of the color shift after 50 cycles of sterilization

|  | CE1 | CE2 | CE3 |
|---|---|---|---|
| ΔE | 43.2 | 11.5 | 17.7 |
| Δb | 36.8 | 11.5 | 17.32 |

TABLE 2b

| Results of the color shift after 50 cycles of sterilization | | | | | | | | | | | |
|---|---|---|---|---|---|---|---|---|---|---|---|
|  | E1 | E2 | E3 | E4 | E5 | E6 | E7 | E8 | E9 | E10 | E11 |
| ΔE | 5.42 | 1.8 | 1.26 | 0.99 | 1.19 | 0.68 | 2.68 | 1.24 | 4.4 | 4.09 | 1.7 |
| Δb | 5.42 | 1.3 | 1.14 | 0.82 | −0.08 | 0.43 | 2.49 | 0.62 | 0.52 | 3.91 | −0.11 |

The invention claimed is:

1. A composition (C) comprising:
(a) a poly(biphenyl ether sulfone) polymer (P) in an amount of at most 99 wt. % and at least 80 wt. % of with respect to the weight of the composition (C);
(b) calcium oxide (CaO) and/or magnesium oxide (MgO), optionally in combination with other metal oxides;
wherein:
the composition (C) does not include a polyether imide polymer;
the CaO, alone or in combination with the MgO and/or with the other metal oxides is in an amount from 1 wt. % to 6 wt. % with respect to the total weight of the composition (C); and
the MgO is in an amount from 1 wt. % to 6 wt. % with respect to the total weight of the composition (C), provided that when the composition (C) does not include the CaO, the amount of the MgO is at least 2 wt. % and up to 6 wt. % with respect to the total weight of the composition (C),
wherein the poly(biphenyl ether sulfone) polymer (P) is a homopolymer or copolymer in which substantially all recurring units of polymer (P) are recurring) selected from the group consisting of formulae (B) to (F), and mixtures thereof:

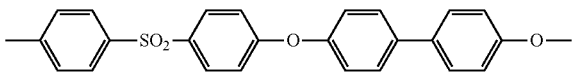
(B)

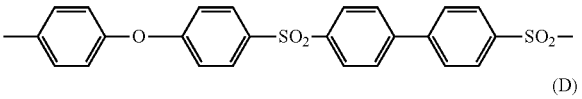
(C)

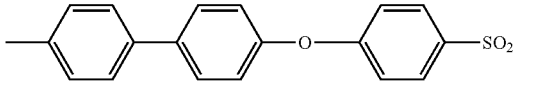
(D)

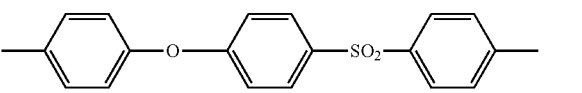
(E)

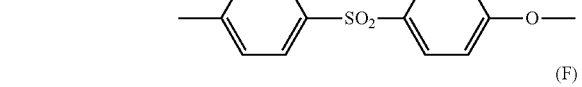
(F)

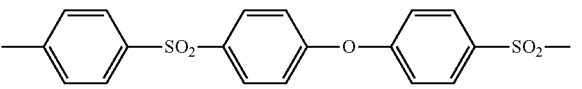

2. The composition according to claim 1, wherein all the recurring units ($R_a$) of the poly(biphenyl ether sulfone) polymer (P) are of formula (B).

3. The composition according to claim 1, further comprising a polymer selected from polyacetals, ethylvinyl acetate, polyolefins, liquid crystal polymers, polyamides, polycarbonates, poly(etherketones), poly(etheretherketones), poly(etherketoneketones), polymethyl methacrylate, polystyrene, polyurethane, polyvinyl chloride, silicone elastomers, polytetrafluoroethylene, and mixtures thereof.

4. The composition according to claim 1 comprising 4% by weight of the CaO.

5. The composition according to claim 1 comprising 2% by weight of the CaO and 2% by weight of the MgO.

6. The composition according to claim 1 comprising 1% by weight of the CaO and 1% by weight of the MgO.

7. The composition according to claim 1 comprising 4% by weight of a mixture of the MgO and $Al_2O_3$.

8. A shaped article comprising the composition of claim 1.

9. The article according to claim 8, which is selected from a medical article, a food handling or food preparation article, and a beverage handling or beverage preparation article.

10. A method for sterilizing the shaped article of claim 8, which comprises submitting the article to hydrogen peroxide gas plasma sterilization.

11. The shaped article according to claim 8, wherein the shaped article has been subjected to at least one hydrogen peroxide gas plasma sterilization process.

12. The composition of claim 1, wherein an article made from the composition (C) and subjected to 50 hydrogen peroxide gas plasma sterilizations of 47 minutes each exhibits an overall color difference (DE) and a change in yellowness (Db) of less than 5.5, wherein DE and Db are calculated according to CIE 1976 (L*, a*, b*) color space indexes measured according to ASTM E308-08.

13. The composition of claim 1, wherein the CaO and/or MgO in the composition (C) have an average particle size up to about 5 microns and a BET surface area of 1.5-160 m²/g.

14. The composition of claim 1, wherein the polymer (P) is in an amount of at least 90 wt. % with respect to the weight of the composition (C).

15. A composition (C) comprising:
(a) a poly(biphenyl ether sulfone) polymer (P);
(b) calcium oxide (CaO) and/or magnesium oxide (MgO), optionally in combination with other metal oxides;
wherein:
the CaO, alone or in combination with the MgO and/or with the other metal oxides is in an amount from 1 wt. % to 6 wt. % with respect to the total weight of the composition (C); and
the MgO is in an amount from 1 wt % to 6 wt. % with respect to the total weight of the composition (C), provided that when the composition (C) does not include the CaO, the amount of the MgO is at least 2% wt. and up to 6 wt. % with respect to the total weight of the composition (C), wherein the CaO and/or MgO in the composition (C) have an average particle size up to about 5 microns and a BET surface area of 1.5-160 m²/g, wherein the poly(biphenyl ether sulfone) polymer (P) is a homopolymer or copolymer in which substantially all recurring units of polymer (P) are recurring units ($R_a$) of formula (A):

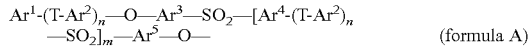   (formula A)

wherein:
Ar¹, Ar², Ar³, Ar⁴, and Ar⁵, equal to or different from each other and at each occurrence, are independently an aromatic mono- or polynuclear cyclic group;

with the proviso that at least one Ar¹ through Ar⁵ is an aromatic moiety comprising at least one biphenylene group;

each of T, equal to or different from each other, is selected from the group consisting of a bond, —CH₂—; —O—; —SO₂—; —S—; —C(CH₃)₂—; —C(CF₃)₂—; —C(=CCl₂)—; —C(CH₃)(CH₂CH₂COOH)—; —N=N—; —R¹C=CR²—; wherein each R¹ and R², independently of one another, is hydrogen or a $C_1$-$C_{12}$-alkyl, $C_1$-$C_{12}$-alkoxy, or $C_6$-$C_{18}$-aryl group; —(CH₂)$_{n'}$— and —(CF2)$_{n'}$—with n'=integer from 1 to 6, or an aliphatic linear or branched divalent group of up to 6 carbon atoms;

n and m, equal to or different from each other, are independently zero or an integer of 1 to 5.

16. The composition of claim 15, wherein the recurring units ($R_a$) in the poly(biphenyl ether sulfone) polymer (P) are selected from the group consisting of formulae (B) to (F), and mixtures thereof:

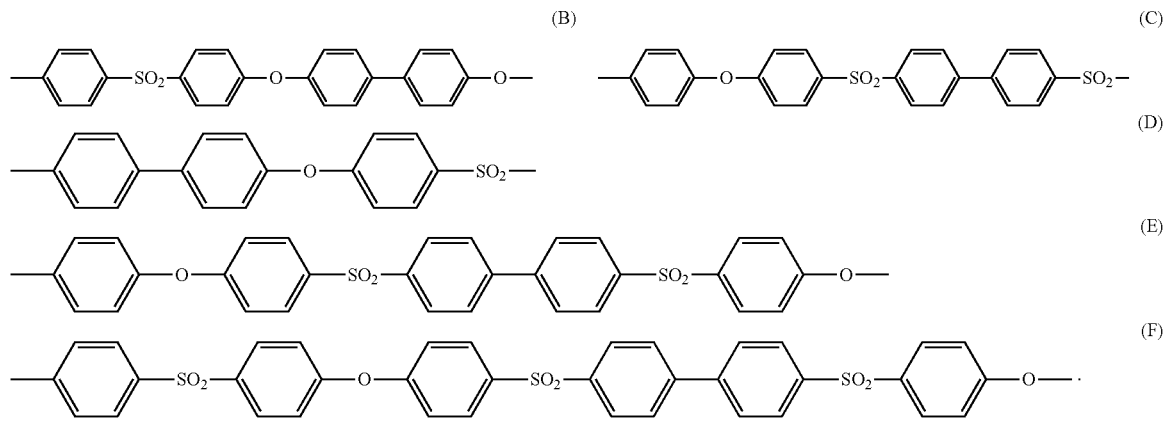

17. The composition according to claim 16, wherein the recurring units ($R_a$) of the poly(biphenyl ether sulfone) polymer (P) are of formula (B).

18. The composition of claim 15, wherein the polymer (P) is in an amount of at most 99 wt. % and at least 80 wt. % with respect to the weight of the composition (C).

19. A shaped article comprising the composition of claim 15, which is selected from a medical article, a food handling or food preparation article, and a beverage handling or beverage preparation article.

20. A method for manufacturing a sterilized shaped article, which comprises submitting the shaped article of claim 18 to hydrogen peroxide gas plasma sterilization.

* * * * *